United States Patent
Chung

(10) Patent No.: US 7,153,311 B2
(45) Date of Patent: Dec. 26, 2006

(54) HAND PIECE FOR MICRODERMABRASION DEVICE

(76) Inventor: Tae-Jun Chung, Hyundai Apt. 825-1401, Jangmi Town, Yatap-Dong, Boondang-Gu, Kyounggi-do (KR)

( * ) Notice: Subject to any disclaimer, the term of this patent is extended or adjusted under 35 U.S.C. 154(b) by 525 days.

(21) Appl. No.: 10/656,370

(22) Filed: Sep. 8, 2003

(65) Prior Publication Data

US 2004/0127914 A1    Jul. 1, 2004

(30) Foreign Application Priority Data

Sep. 6, 2002    (KR) .................... 20-2002-0026678

(51) Int. Cl.
*A61B 17/50* (2006.01)
(52) U.S. Cl. .................................... 606/131
(58) Field of Classification Search ........... 606/128, 606/131, 159, 107; 604/117, 119, 289, 290, 604/303, 313, 542, 902
See application file for complete search history.

(56) References Cited

U.S. PATENT DOCUMENTS 6,241,739 B1    6/2001    Waldron
6,500,183 B1    12/2002    Waldron

*Primary Examiner*—Anhtuan T. Nguyen
*Assistant Examiner*—Melanie Tyson
(74) *Attorney, Agent, or Firm*—Greenblum & Bernstein, P.L.C.

(57) ABSTRACT

The present invention relates to a hand piece used for vacuum suction type dermabrasion apparatus. The hand piece includes a replaceable dermabrasion tip installed into a tubular housing. The dermabrasion tip consists of a cylindrical upper stage and a cylindrical lower stage, the upper has a smaller diameter than the lower stage and an abrasive surface formed on the upper surface of the upper stage, and the lower stage has a diameter generally fitting to the diameter of the hollow and a plurality of suction holes are formed through the lower stage around the periphery of the upper stage.

3 Claims, 6 Drawing Sheets

HAND PIECE FOR MICRODERMABRASION DEVICE

TECHNICAL FIELD

The present invention generally relates to a hand piece used for microdermabrasion device. Particularly, the present invention relates to a hand piece including a replaceable dermabrasion tip.

BACKGROUND OF THE INVENTION

Dermabrasion is a treatment for removing dead cells from the outermost layer of skin and cleaning blocked pores. Derambrasion treatment has been widely used for therapeutic and cosmetic purposes. Conventionally dermabrasion was conducted using cleansing cream or make-up remover containing abrasive component.

Recently a technique of abrading the skin surface by rubbing a device having an abrasive surface against skin while sucking up the dislodged skin cells. This type of dermabrasion device is disclosed in U.S. Pat. Nos. 6,241,739 and 6,500,138 issued to Waldron. FIG. 1 shows the overall structure of the deramabrasion device taught by Waldron. The system includes a vacuum pump 24, and a gauge 14 to measure the level of vacuum and a valve 16 to adjust the vacuum are connected to the vacuum pump 24. A filter assembly 18 is connected to the vacuum pump 24 through a vacuum line 36. Attached to the filter assembly 18 is a hollow tube 26 or a wand assembly upon which the treatment tip 22 is mounted. The filter assembly 18 collects the loosened skin tissue and prevents the skin tissue or collected housing fluids and oils from entering the vacuum pump. When a vacuum is applied through the tube 26 to the treatment tip 22, the tip 22 is brought into contact with skin, the vacuum causing the skin to be pressed against an abrasive surface on the end of the treatment tip. As the tip is manually moved across skin the abrasive surface abrades the epidermis dislodging cells from the surface. The vacuum causes the dislodged cells to flow into the wand assembly 26.

FIG. 2 illustrates a typical structure of a treatment tip being used in the dermabrasion device as shown in FIG. 1. The treatment tip 22 has a tubular shape and preferably made of metallic material such as stainless steel. A connector tube 32 is inserted into one end of the treatment tip 22. The connector tube 32 is used to connect the treatment tip to the tube 26 which is in turn connected to the filter assembly 18. The other end of the treatment tube is formed with an abrasive surface 48. The abrasive surface may be formed by using various methods as follows: (1) coating diamond particles with nickel bonding; (2) coating abrasive material such as aluminum oxide; and (3) surface machining.

The dermabrasion device as describe above has several problems. First, the abrasive surface is integrally formed on the treatment tip. Since the tip is reused for many treatments without replacement, dislodged skin cells may remain adhering to the abrasive surface even after cleaning the treatment tip. This may cause harmful hygienic effects such as infection of skin disease. Second, the skin cells dislodged from patient's skin is absorbed into the hole formed at the center of the treatment tip. The skin cells dislodged by the periphery of the abrasive surface may not be effectively absorbed into the hole since the vacuum pressure applied to the center hole of the treatment tip tend to be significantly reduced when reaching the periphery of the treatment tip.

SUMMARY OF THE INVENTION

One objective of the present invention is to provide a hand piece for a dermabrasion device having a replaceable dermabrasion tip. Since the dermabrasion tip contacting and abrading patient's skin surface is replaced for each treatment, it may prevent the hygienic problem of the conventional apparatus. Further object of the present invention is to provide a hand piece which can effectively absorb the dislodged skin cells during operation. According to the present invention, vacuum pressure is formed to surround the dermabrasion tip so that all of the dislodged skin cells are effectively absorbed in the filter assembly.

In order to achieve the objectives, the present invention provides a hand piece used for a suction type dermabrasion device comprising a housing having a tubular shape with a hollow formed therein; a connecting tube connected to one side of the housing to apply vacuum pressure to the inside of the housing; a spring inserted into the hollow of the housing; and a dermabrasion tip installed in the hollow of the housing to be elastically supported by the housing. The dermabrasion tip consists of a cylindrical upper stage and a cylindrical lower stage, the upper has a smaller diameter than the lower stage and an abrasive surface formed on the upper surface of the upper stage, and the lower stage has a diameter generally fitting to the diameter of the hollow and a plurality of suction holes are formed through the lower stage around the periphery of the upper stage.

BRIEF DESCRIPTION OF THE DRAWINGS

The embodiments of the present invention will be explained with reference to the accompanying drawings, in which.

DETAILED DESCRIPTION OF THE INVENTION

Figure 1:
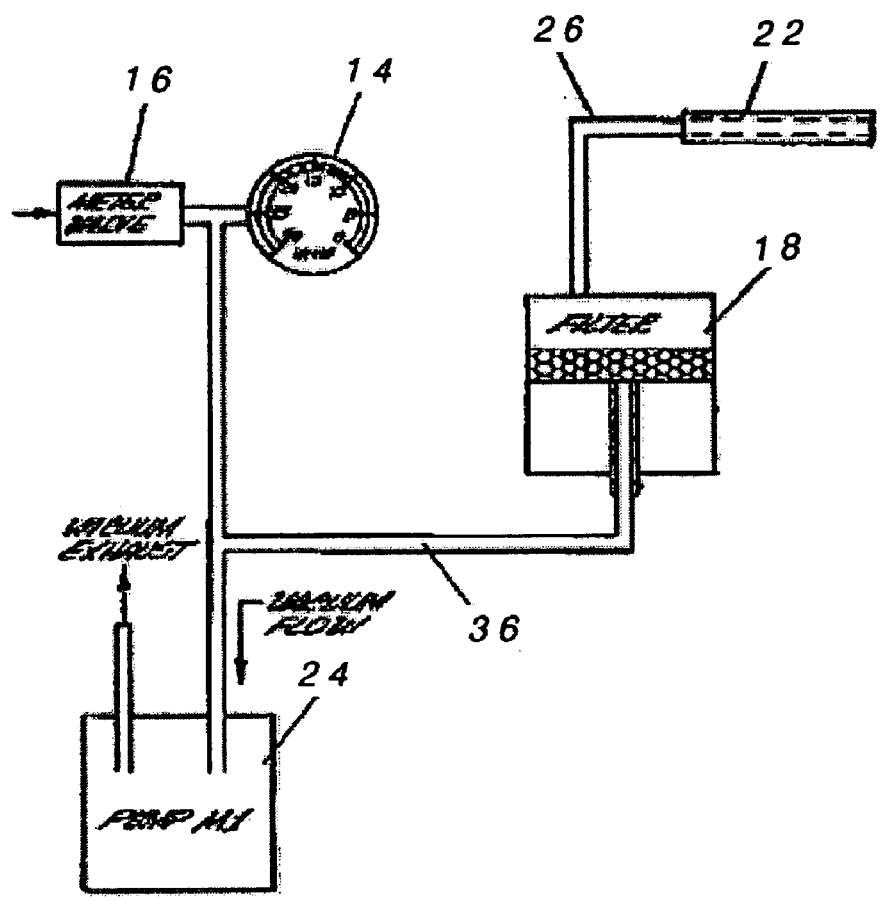
FIG. 1 is a schematic drawing showing the general structure and operation of the dermabrasion device according to prior art.
Figure 2:
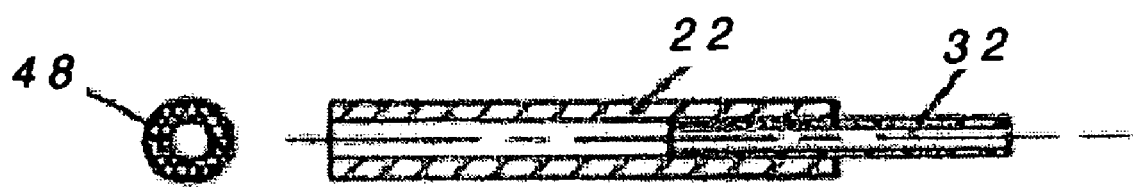
FIG. 2 is a diagram illustrating a treatment tip used in the dermabrasion device as shown in FIG. 1.

Hereinafter, preferred embodiments according to the present invention will be explained in detail with reference to the accompanying drawings. In the accompanying drawings, same reference numerals are used to indicate the corresponding elements.

Figure 3:
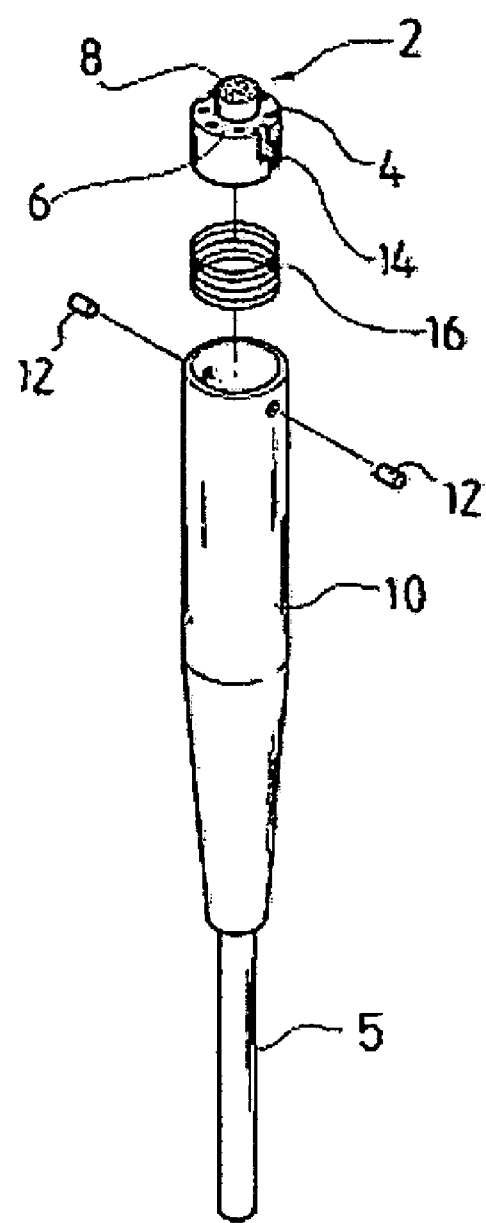
FIG. 3 is an exploded perspective view of a dermabrasion hand piece according to the present invention.
Figure 4:
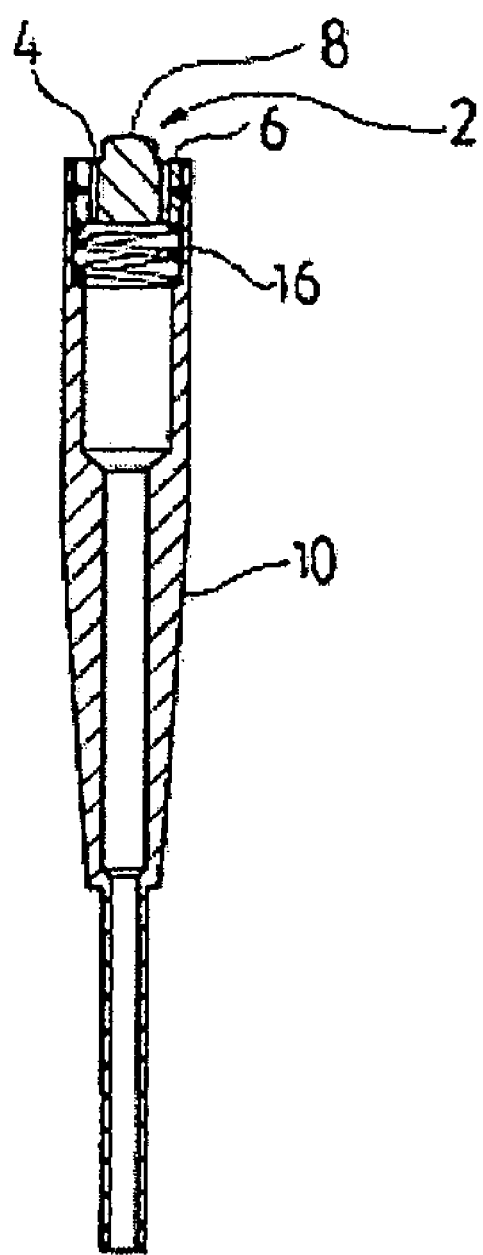
FIGS. 4 and 5 are cutaway views of the dermabrasion hand piece according to the present invention.
Figure 5:
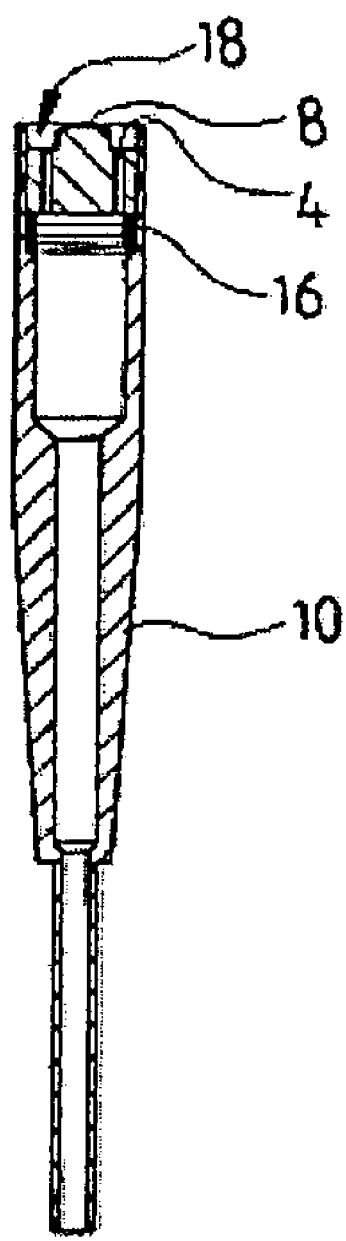

Referring to FIGS. 3 to 5, the hand piece according to the present invention comprises a housing 10 having a generally tubular shape with a hollow formed therein. The housing is preferably formed with metallic material such as stainless steel. A connecting tube 5 is formed at one end of the housing 10. The connecting tube 5 may be integrally formed with the housing, or may be detachably connected to the housing. Though the connecting tube, vacuum is applied to the inside of the housing connected thereto. Preferably, as shown in the drawings, at least a portion of the housing has a tapered shape to make it easy to grip.

A spring 16 is inserted into the hollow of the housing 10 and, as shown in FIGS. 4 and 5, one end of the spring engages with a step formed within the hollow of the housing. Then a dermabrasion tip 2 is inserted into the hollow to sit over the spring 16. The dermabrasion tip 2 has a generally cylindrical shape consisting of two stages. The upper stage has a smaller diameter and its upper surface is formed with an abrasive surface 8 which is used to abrade patient's skin. The abrasive surface 8 of the upper stage may be formed by using any conventional methods as described above. The lower stage 6 has a larger diameter snugly fitting to the diameter of the hollow of the housing, and a plurality of suction holes 4 are formed through the lower stage 6 around the periphery of the upper stage. The number and the size of the suction holes may be adjusted according to the design requirements. The upper stage and the lower stage are preferably formed as one body with a suitable material such as stainless steel and plastic.

A pair of mounting grooves 14 are formed at opposing locations on the side of the lower stage 6. When the dermabrasion tip 2 is inserted into the housing 10, the dermabrasion tip 2 is installed at a predetermined position by engaging a pair of pins 12 with the mounting grooves 14. Preferably, as shown in FIG. 4, the dermabrasion tip 2 is mounted at a position where its upper stage protrudes from the hollow of the housing. At the position, the dermabrasion tip 2 is biased upward by the resilient force of the spring 16. When the hand piece is depressed against patient's skin, the abrasive surface 8 of the dermabrasion tip 2 becomes to contact with the skin and the dermabrasion tip 2 is depressed into the housing as shown in FIG. 5. As the pins 12 are engaged with the mounting grooves 14 to allow sliding motion, the dermabrasion tip 2 may move into the hollow when depressed against skin.

Figure 6:
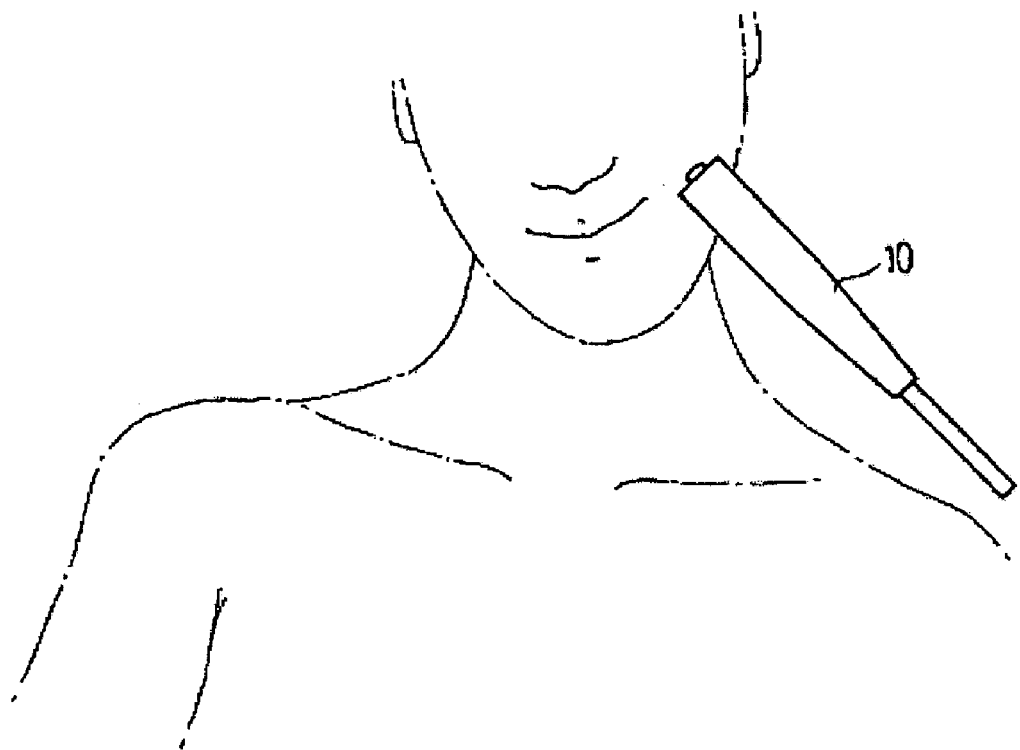
FIG. 6 is a drawing showing a method using the hand piece according to the present invention.

During treatment as shown in FIG. 6, the abrasive surface is pressed against the patient's skin. Thus, while rubbing the hand piece to the skin, the deal cells of skin is abraded by the abrasive surface formed on the dermabrasion tip. When the dermabrasion tip is depressed against skin, as shown in FIG. 5, a vacuum space 18 is formed to surround the upper stage of the dermabrasion tip 2. Therefore, all of the dislodged cells are absorbed in the suction holes without leaving any fall out.

According to the present invention, without replacing the entire hand piece, only the dermabrasion tip can be easily replaced for each treatment. Releasing the pin, a used dermabrasion tip may be removed and a new dermabrasion tip can be mounted by a method as described above. Since the unit price of the dermabrasion tip is cheaper compared to the price of the entire hand piece, the present invention may ensure hygienic dermabrasion treatment at a reasonable cost.

Although the present invention has been described with respect to the preferred embodiments thereof, the present invention is not limited to the embodiments. It should be understood that a person having an ordinary skill in the art to which the present invention pertains can make various modifications and changes to the present invention without departing from the spirit and scope of the invention defined by the appended claims.

The present disclosure relates to subject matter contained in priority Korean Patent Application No. 20-2002-0026678, filed on Sep. 6, 2002, the contents of which is herein expressly incorporated by reference in its entirety.

What is claimed is:

1. A hand piece used for a suction type dermabrasion device comprising:
   a housing having a tubular shape with a hollow formed therein;
   a connecting tube connected to one side of the housing to apply vacuum pressure to the inside of the housing;
   a spring inserted into the hollow of the housing; and
   a dermabrasion tip installed in the hollow of the housing to be elastically supported by the housing,
   wherein the dermabrasion tip consists of a cylindrical upper stage and a cylindrical lower stage, the upper has a smaller diameter than the lower stage and an abrasive surface formed on the upper surface of the upper stage, and the lower stage has a diameter generally fitting to the diameter of the hollow and a plurality of suction holes are formed through the lower stage around the periphery of the upper stage.

2. A hand piece used for a suction type dermabrasion device according to claim 1, wherein a pair of mounting grooves are formed at opposing locations on the side of the lower stage, and the dermabrasion tip is installed in the housing by engaging a pair of pins with the mounting grooves through the housing.

3. A hand piece used for a suction type dermabrasion device according to claim 1, wherein the abrasive surface of the dermabrasion tip is formed by using any one of the methods of coating diamond particles, coating aluminum oxide, and surface machining.

* * * * *